United States Patent
Hecker et al.

(10) Patent No.: US 7,153,842 B2
(45) Date of Patent: Dec. 26, 2006

(54) FLORFENICOL PRODRUG HAVING IMPROVED WATER SOLUBILITY

(75) Inventors: Scott Hecker, Del Mar, CA (US); Sunil V. Pansare, St. Johns (CA); Tomasz W Glinka, Cupertino, CA (US)

(73) Assignee: Schering-Plough Animal Health Corporation, Kenilworth, NJ (US)

( * ) Notice: Subject to any disclaimer, the term of this patent is extended or adjusted under 35 U.S.C. 154(b) by 101 days.

(21) Appl. No.: 11/016,794

(22) Filed: Dec. 20, 2004

(65) Prior Publication Data

US 2005/0182031 A1   Aug. 18, 2005

Related U.S. Application Data

(60) Provisional application No. 60/532,227, filed on Dec. 23, 2003.

(51) Int. Cl.
*A61K 31/661* (2006.01)
*C07F 9/141* (2006.01)

(52) U.S. Cl. .......................... 514/119; 558/170
(58) Field of Classification Search ................ 514/119; 558/170
See application file for complete search history.

(56) References Cited

U.S. PATENT DOCUMENTS 2,776,992 A   1/1957   Gregory
4,235,892 A   11/1980  Nagabhushan
5,352,832 A   10/1994  Wu et al.
2004/0082553 A1   4/2004   Boojamra et al.
2005/0182138 A1   8/2005   Shuster et al.

FOREIGN PATENT DOCUMENTS

EP        0 014 437 A2    8/1980
WO    WO 03/077828 A2    9/2003
WO    WO 2005/009429 A1   2/2005

OTHER PUBLICATIONS

Bolton, Lance F., et al., "Detection of Multidrug-Resistant . . . ," Journal of Clinical Microbiology 37(5):1348-1351 (May 1999).
Cloeckaert, Axel, et al., "Nonenzymatic Chloramphenicol Resistance Mediated . . . ," Antimicrobial Agents and Chemotherapy 45(8):2381-2382 (Aug. 2001).
Keyes, Kathleen, et al., "Detection of Florfenicol Resistance Genes . . . ," Antimicrobial Agents and Chemotherapy 44(2):421-424 (Feb. 2000).
Kim, Eun-Heul, et al., "Sequence Analysis of the Florfenicol Resistance . . . ," Microbiol. Immunol. 40(9):665-669 (1996).
PCT International Search Report dated Jun. 28, 2005 for corresponding PCT Application No. PCT/US2004/042591.

*Primary Examiner*—Kamal A. Saeed
*Assistant Examiner*—Jason M. Nolan

(57) ABSTRACT

The present invention discloses phosphate esters of florfenicol (prodrugs) and florfenicol analogs having superior water solubility that are hydrolyzed to florfenicol or the respective florfenicol analog in vivo, upon administration to an animal.

30 Claims, 4 Drawing Sheets

FLORFENICOL PRODRUG HAVING IMPROVED WATER SOLUBILITY

CROSS-REFERENCE TO RELATED APPLICATIONS

This application is a non-provisional application that claims priority under 35 U.S.C. § 119(e) of provisional application U.S. Ser. No. 60/532,227 filed Dec. 23, 2003, the contents of which are hereby incorporated by reference in their entireties.

FIELD OF THE INVENTION

The present invention is directed to phosphate esters of florfenicol, including a florfenicol prodrug having superior water solubility, and phosphate esters of florfenicol analogs.

BACKGROUND OF THE INVENTION

Florfenicol is a structural analog of thiamphenicol, which in turn is a derivative of chloramphenicol [see, e.g., U.S. Pat. No. 4,235,892, U.S. Pat. No. 5,352,832, the contents of which are hereby incorporated by reference in their entireties].

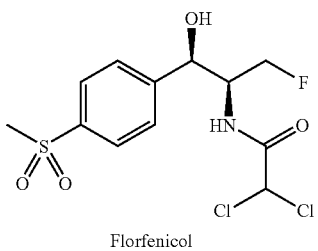
Florfenicol

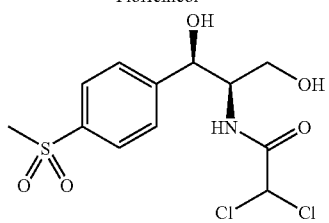
Thiamphenicol

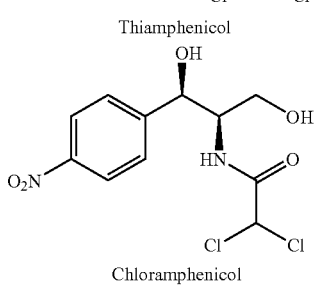
Chloramphenicol

Florfenicol is a broad spectrum antibiotic with activity against many gram-negative and gram-positive bacteria, including utility in the prevention and treatment of bacterial infections due to susceptible pathogens in birds, reptiles, fish, shellfish and mammals. One of florfenicol's primary uses is in the treatment of pneumonia and associated respiratory infections in cattle (often referred to generically as Bovine Respiratory Disease or BRD) caused by *Mannhemia haemolytica, Pasturella multocida* and/or *Haemophilus somnus*, also known as *Histophilus somni*. It is also indicated in the treatment of: pododermatitis in cattle caused by *Fusobacterium necrophorum* and *Bacterioides melaninogenicus*; swine respiratory disease caused by *Pasteurella multocida, Actinobacillus pleuropneumoniae, Streptococcus suis, Salmonella cholerasuis* and/or *Mycoplasma* spp.; colibacillosis in chickens caused by *Escherichia coli*; enteric septicemia in catfish caused by *Edwardsiella ictaluri*; and furunculosis in salmon caused by *Aeromonas salmonicida*. Other genera of bacteria that have exhibited susceptibility to florfenicol include *Enterobacter, Klebsiella, Staphylococcus, Enterococcus, Bordetella, Proteus* and *Shigella*. In particular, chloramphenicol-resistant strains of organisms, such as *K. pneumoniae, E. cloacae, S. typhus* and *E. coli*, are susceptible to florfenicol.

Florfenicol is most often administered to subjects which can benefit from its advantages either orally or parenterally, the latter being primarily intramuscular or intravenous. Due to its very low water solubility (approximately one mg/mL), organic solvents must be added to achieve the desired product concentration in a commercial formulation. For example, in NUFLOR® (veterinary-labeled florfenicol formulation in the United States and Canada), the organic solvents N-methylpyrrolidinone, propylene glycol and/or polyethylene glycol are used to afford florfenicol solubility of 300 mg/mL. Unfortunately, when administered parenterally, these solvents often cause significant localized irritation. Therefore, there is a need for a more water-soluble form of florfenicol.

The citation of any reference herein should not be construed as an admission that such reference is available as "Prior Art" to the instant application.

SUMMARY OF THE INVENTION

The present invention therefore, provides a water-soluble form of florfenicol that has substantially greater aqueous solubility than florfenicol itself. Preferably a water-soluble form of florfenicol of the present invention is also a prodrug that rapidly and efficiently converts to florfenicol in vivo. One aspect of the present invention therefore provides a florfenicol phosphate ester (e.g., a florfenicol prodrug) having the chemical structure:

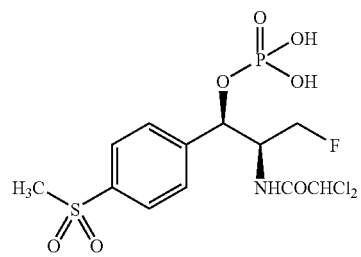

The present invention further provides salts of this florfenicol phosphate ester. Such salts may be useful in the stable storage of the florfenicol phosphate esters. Preferably, the florfenicol phosphate ester salts comprise pharmaceutically-acceptable counterions. In a particular embodiment, the acids and pharmaceutically-acceptable florfenicol phosphate ester salts of the present invention may be depicted as:

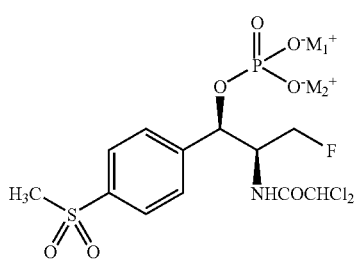

Formula I wherein $M_1^+$ and $M_2^+$ are independently selected to be either $H^+$ or a pharmaceutically-acceptable mono-cation, or alternatively, $M_1^+$ and $M_2^+$ can be taken together as a pharmaceutically-acceptable di-cation.

In one embodiment of the present invention, $M_1^+$ and $M_2^+$ are independently selected to be $H^+$, $Na^+$, $NH_4^+$, or $K^+$. In a particular embodiment of this type, $M_1^+$ and $M_2^+$ are respectively, $H^+$ and $Na^+$. In another particular embodiment of this type, $M_1^+$ and $M_2^+$ are both $Na^+$. In yet another embodiment, $M_1^+$ and $M_2^+$ taken together are $Ca^{+2}$. In still another embodiment, $M_1^+$ and $M_2^+$ taken together are $Mg^{+2}$.

In yet another embodiment of the present invention, $M_1^+$ and $M_2^+$ are independently selected to be either $H^+$ or a protonated amine. In another embodiment of the present invention, $M_1^+$ and $M_2^+$ are respectively, $H^+$ and a protonated amine comprising the chemical formula $NR^1R^2R^3H^+$. In still another embodiment, $M_1^+$ and $M_2^+$ are both a protonated amine comprising the chemical formula $NR^1R^2R^3H^+$. With regard to the protonated amine comprising the chemical formula $NR^1R^2R^3H^+$: $R^1$, $R^2$, and $R^3$ are independently selected to be either H, methyl, ethyl, propyl, isopropyl, $-CH_2CH_2OH$ and $-CH_2C(CH_2OH)_3$. Alternatively, $R^1$ is as provided above, but $R^2$ and $R^3$ are linked to form a five or six membered ring. In a specific embodiment of this type, the ring is pirolidine, piperidine or morpholine.

Examples of amine cations of the present invention include, but are not limited to:

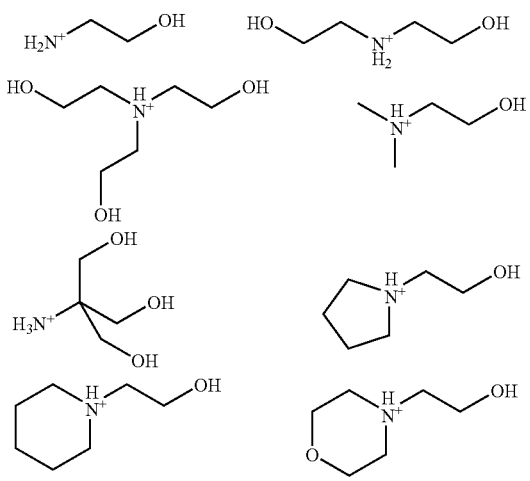

In still another embodiment $M_1^+$ and $M_2^+$ taken together form a bis-protonated diamine.

Examples of bis-protonated diamines of the present invention include:

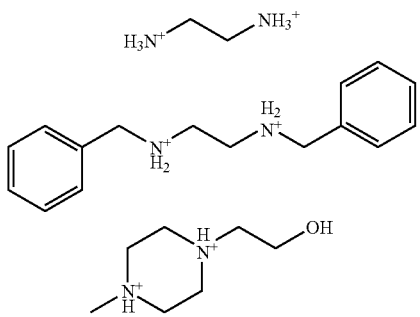

In yet another embodiment $M_1^+$ and $M_2^+$ comprise respectively, $H^+$ and a mono-cationic form of a dibasic aminoacid. In a particular embodiment of this type, the mono-cationic form of the dibasic aminoacid comprises one of the following two chemical formulas:

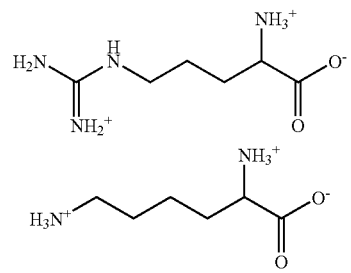

In still another embodiment $M_1^+$ and $M_2^+$ taken together comprise a di-cationic form of a dibasic aminoacid. In a particular embodiment of this type, the di-cationic form of the dibasic aminoacid comprises one of the two following chemical formulas:

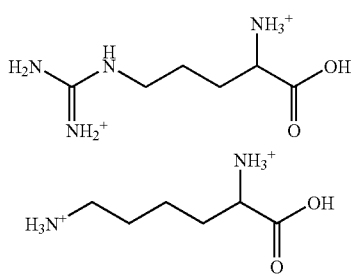

In yet another embodiment of the present invention, $M_1^+$ and $M_2^+$ are independently selected to be either $H^+$, meglumine, benzocaine, or procaine. In a particular embodiment of this type, either $M_1^+$ and $M_2^+$ are $H^+$, while the other is either meglumine, benzocaine or procaine.

In still another embodiment, the present invention provides a formulation that comprises Formula I as a mixture of two or more salts. In a particular embodiment of this type, for one salt, $M_1^+$ or $M_2^+$ is $H^+$, whereas the other is a specific counterion, wherein for the second salt, both $M_1^+$ and $M_2^+$ are that specific counterion. In a related embodiment, $M_1^+$ and $M_2^+$ of the first salt are identical counterions, but not $H^+$, whereas $M_1^+$ and $M_2^+$ of the second salt are also identical counterions, but are neither $H^+$, nor the specific counterion of the first salt. In yet another embodiment, the formulation comprises Formula I as a mixture of two or more salts, and all of the counterions of the different salts are selected independently. In a preferred embodiment, the counterions in these formulations are disclosed herein.

The present invention further provides phosphate esters of florfenicol analogs (including phosphate esters of chloramphenicol and thiamphenicol) that also can be useful as antibiotics and/or prodrugs of antibiotics. The present invention further provides salts of these phosphate esters of the florfenicol analogs, preferably salts comprising the counterions provided herein. One appropriate family of florfenicol analogs has recently been synthesized and characterized [U.S. 20040082553, WO03/077828, the contents of which are hereby incorporated by reference in their entireties]. The phosphate esters of these florfenicol analogs and salts thereof, can be prepared and then employed as antibiotics and/or prodrugs of antibiotics through the teachings provided herein, in view of the teachings of U.S. 20040082553 and WO03/077828.

In a particular embodiment, a phosphate ester of a florfenicol analog of the present invention comprises the chemical structure of:

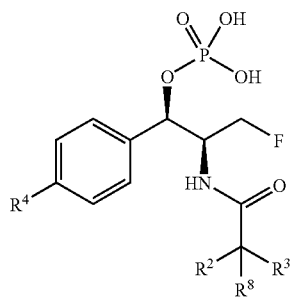

wherein $R^2$ and $R^3$ are independently selected from the group consisting of hydrogen, (1C–4C)alkyl, halo, —$CF_3$, —$NH_2$, —CN and $N_3$;

wherein $R^4$ is selected from the group consisting of:

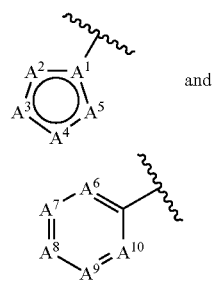

wherein $A^1$ is carbon or nitrogen, and carbon atoms in the ring are independently substituted with an entity selected from the group consisting of hydrogen, (1C–4C)alkyl, (3C–6C)cycloalkyl, (1C–4C)alkylO—, —$CF_3$, —OH, —CN, halo, (1C–4C)alkylSO—, (1C–4C)alkylSO$_2$—, $NH_2SO_2$—, (1C–4C)alkylNHSO$_2$—, (1C–4C)alkyl)$_2$NSO$_2$—, —$NH_2$, (1C–4C)alkylNH—, ((1C–4C)alkyl)$_2$N—, (1C–4C)alkylSO$_2$NH—, (3C–6C)cycloalkylC(O)—, (1C–4C)alkylOC(O)—, (1C–4C)alkylC(O)NH—, —C(O)NH$_2$, (1C–4C)alkylNHC(O)— and ((1C–4C)alkyl)$_2$NC(O)—, wherein any of the alkyl groups within the substituents may be unsubstituted or substituted with a group selected from halo and hydroxy;

wherein $A^2$, $A^3$, $A^4$, and $A^5$ are independently selected from the group consisting of carbon, nitrogen, oxygen and sulfur, provided that at least one of $A^1$–$A^5$ is not carbon, that the total number of nitrogen, oxygen and sulfur atoms in the ring does not exceed 4 and that the ring is aromatic; and wherein if $A^1$ is carbon and the ring does not contain oxygen or sulfur, one of the nitrogen atoms may optionally be substituted with an entity selected from the group consisting of (1C–4C)alkyl, (1C–4C)alkylSO$_2$— and —$NH_2$; and wherein $A^6$, $A^7$, $A^8$, $A^9$ and $A^{10}$ are independently selected from the group consisting of carbon, nitrogen and

provided that only one of $A^6$–$A^{10}$ at a time can be

and that one, two, or three of the $A^6$–$A^{10}$ atoms are nitrogen; and wherein the carbon atoms in the ring are independently substituted with an entity selected from the group consisting of hydrogen, (1C–4C)alkyl, (3C–6C)cycloalkyl, (1C–4C)alkylO—, —$CF_3$, —OH, —CN, halo, (1C–4C)alkylSO—, (1C–4C)alkylSO$_2$—, $NH_2SO_2$—, (1C–4C)alkylNHSO$_2$—, ((1C–4C)alkyl)$_2$NSO$_2$—, —$NH_2$, (1C–4C)alkylNH—, ((1C–4C)alkyl)$_2$N—, (1C–4C)alkylSO$_2$NH—, (1C–4C)alkylC(O)—, (3C–6C)cycloalkylC(O)—, (1C–4C)alkylOC(O)—, (1C–4C)alkylC(O)NH—, —C(O)NH$_2$, (1C–4C)alkylNHC(O)—, ((1C–4C)alkyl)$_2$NC(O)— and —OCH$_2$O—, wherein the oxygen atoms with the —OCH$_2$O— substituent being bonded to adjacent ring carbon atoms, and wherein any of the alkyl groups within any of the substituents may be unsubstituted or substituted with a group selected from halo and hydroxy; and wherein $R^8$ is hydrogen in all compounds, except when $R^2$ and $R^3$ are both F, in which case $R^8$ is hydrogen or F; and, the compound is either a racemate having the relative stereochemistry shown or is substantially enantiomerically pure and has the absolute stereochemistry shown. In a preferred embodiment of this type, the phosphate ester of the florfenicol analog can serve as a prodrug of the corresponding florfenicol analog.

All of the forms of the florfenicol phosphate ester of the present invention (e.g., florfenicol prodrugs) as well as all of the forms of the phosphate esters of the florfenicol analogs may be prepared in pharmaceutical compositions comprising one or more pharmaceutically-acceptable carriers (e.g., solvents), and/or one or more pharmaceutically-acceptable excipients. In addition, the present invention also provides all of the forms of the florfenicol phosphate ester and all of the forms of the phosphate esters of the florfenicol analogs of the present invention in an isolated and/or purified form.

Therefore, the present invention provides a pharmaceutical composition comprising a florfenicol prodrug (or a phosphate ester of a florfenicol analog) of the present invention in a pharmaceutically acceptable carrier. In a particular embodiment, the pharmaceutical composition comprises a mixture of two or more salts of the florfenicol prodrug. In a related embodiment, the pharmaceutical composition comprises a mixture of two or more salts of a phosphate ester of a florfenicol analog.

In one embodiment the pharmaceutically acceptable carrier comprises an organic solvent. In a particular embodiment of this type, the organic solvent is an aprotic solvent. In a related embodiment, the pharmaceutically acceptable carrier is a mixture of an aqueous solution and an organic solvent. In a preferred embodiment, the pharmaceutically acceptable carrier is an aqueous solution. In an embodiment of this type, the pH of the aqueous solution is between pH 3.5 and pH 6.5. In another embodiment the pH of the aqueous solution is between pH 4.0 and pH 6.0. In still another embodiment, the pH of the aqueous solution is between pH 4.5 and pH 5.5. In a particular embodiment, the pH of the solution is between pH 4.2 and pH 4.8.

In a preferred embodiment of the present invention, a pharmaceutical composition of the present invention comprises a mixture of a salt form of the florfenicol phosphate ester with an acid form of the florfenicol phosphate ester. In one such embodiment, the molar ratio of the base (e.g., a free amine) that is combined with the acid form of the florfenicol phosphate ester is in the range of 0.6–1.4. In another embodiment, the molar ratio is in the range of 0.8–1.2. In still another embodiment the molar ratio is in the range of 0.9–1.1.

The florfenicol phosphate ester, e.g., florfenicol prodrug, or phosphate esters of the florfenicol analogs, and/or salts of either, according to the present invention may be used to treat or prevent a bacterial infection (e.g., those listed above) by administering to a subject in need thereof, a therapeutically- or prophylactically-effective amount of a pharmaceutical composition comprising the florfenicol prodrug or salt thereof, and/or phosphate ester of a florfenicol analog or salt thereof.

In a particular embodiment, a pharmaceutical composition of the present invention is administered orally. In a particular embodiment of this type, a pharmaceutical composition of the present invention is in an aqueous solution. In one such embodiment, the pharmaceutical composition is placed into a liquid to be ingested by the subject, e.g., into its drinking water.

In another embodiment of the present invention, the pharmaceutical composition is administered parenterally. Parenteral administration may involve intramuscular or intravenous injection. Parenteral administration may also involve subcutaneous injection.

The florfenicol phosphate ester (e.g., florfenicol prodrug) and/or salt thereof of the present invention, and phosphate esters of the florfenicol analogs and/or salts thereof of the present invention, may be prepared by a number of methods. In a preferred embodiment, a florfenicol produg is prepared by reacting florfenicol with di-tert-butylphosphoramidite in the presence of tetrazole, in a first suitable solvent, yielding a first intermediate. Next, an oxidant is added in a second suitable solvent to the first intermediate, yielding a second intermediate. After isolating the second intermediate, the second intermediate is dissolved in a third suitable solvent. The second intermediate is then reacted with trifluoroacetic acid to yield a florfenicol phosphate in its acid form. The acid form of florfenicol phosphate can subsequently be isolated. In a particular embodiments one or more of the first, second, and/or third suitable solvent(s) is(are) an aprotic solvent(s).

The isolated acid form of florfenicol phosphate ester then can be added to (or combined with) an aqueous solution of a base that comprises a pharmaceutically-acceptable cation or di-cation. A salt form of the florfenicol prodrug can then be isolated, yielding an isolated florfenicol prodrug with a pharmaceutically-acceptable cation or dication.

In one embodiment of the process of preparing the florfenicol prodrugs of the present invention, the first suitable solvent comprises tetrahydrofuran. In another embodiment, the oxidant used is m-chloroperbenzoic acid. In still another embodiment, the second suitable solvent is dichloromethane. In a particular embodiment, isolating the second intermediate comprises flash column chromatography. In yet another embodiment, the third suitable solvent comprises dichloromethane. In still another embodiment, the pharmaceutically-acceptable cation is $Na^+$. In yet another embodiment, the pharmaceutically-acceptable cation is a protonated amine. In still another embodiment, the pharmaceutically-acceptable di-cation is a bis-protonated diamine.

DETAILED DESCRIPTION OF THE INVENTION

Figure 1:
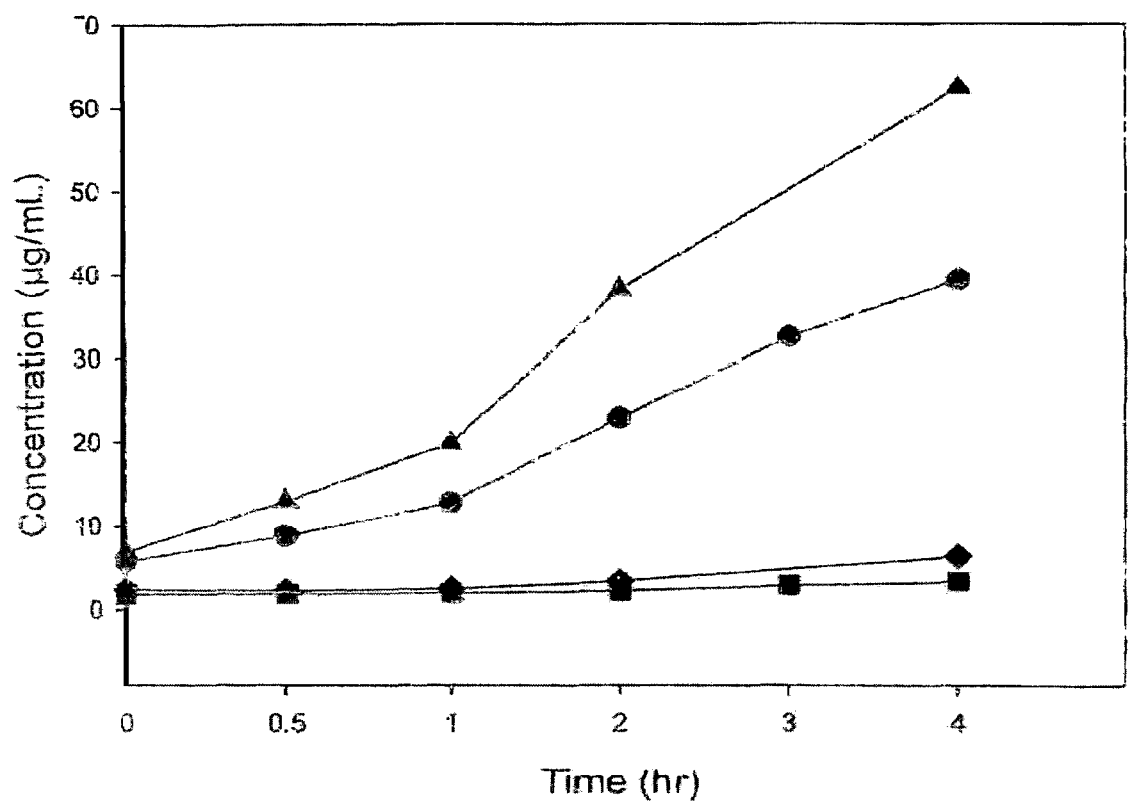
FIG. 1 shows a plot of the rate and degree of conversion to florfenicol of the phosphate ester of the present invention as compared to a glutarate ester in rat and bovine serum. (triangles—phosphate ester in bovine serum; circles, phosphate ester in rat serum; diamonds—glutarate ester in bovine serum; squares—glutarate ester in rat serum)

Accordingly, the present invention provides an esterified form of florfenicol (e.g., a florfenicol prodrug) or an esterified form of a florfenicol analog. Such esterified forms are extremely soluble in water and can be used to treat and/or prevent bacterial infections. When the water-soluble forms of florfenicol or a florfenicol analog are administered to a subject, the esterified form of florfenicol or the florfenicol analog is efficiently converted to free florfenicol, or the free florfenicol analog, respectively.

In order to more fully appreciate the instant invention, the following definitions are provided.

As used herein, a "pharmaceutical composition" refers to a formulation of a phosphate ester of florfenicol, including salts thereof, of the present invention (e.g., a florfenicol prodrug) or a formulation of a phosphate ester of florfenicol analog, including salts thereof, of the present invention, with a pharmaceutically acceptable excipient, and/or carrier. In a particular embodiment, the carrier is a solvent (e.g., water).

An "excipient" refers to an inert substance added to a pharmacological composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The term "therapeutically-effective amount," as used herein, refers to that amount of a prodrug of the present invention that will hydrolyze sufficiently rapidly and in sufficient amounts to provide florfenicol (or florfenicol analog) in a concentration at which it can relieve to some extent one or more of the symptoms of a bacterial infection in a subject. In particular embodiment, a therapeutically-effective amount refers to that amount of a florfenicol phosphate ester of the present invention that, when administered to a subject, delivers florfenicol to a subject in a sufficient plasma concentration to: (1) reduce, and preferably eliminate, the population of bacterial cells in a subject's body; (2) inhibit (i.e., slow, or preferably stop) proliferation of the bacterial cells; (3) inhibit (i.e., slow, preferably stop) spread of the bacterial infection; and/or (4) relieve (preferably eliminate) one or more symptoms associated with the infection.

The term "prophylactically-effective amount" refers to the amount of a prodrug of florfenicol, or florfenicol analog, of the present invention, that provides, upon hydrolysis, a sufficient plasma concentration of florfenicol, or the corresponding florfenicol analog, to: (1) maintain a reduced level of a population of bacterial cells achieved by a previously-administered therapeutically-effective amount of the prodrug or some other appropriate drug; (2) maintain the level of inhibition of the proliferation of bacterial cells achieved by administration of a therapeutically-effective amount of a drug; (3) maintain the degree of inhibition of the spread of the infection achieved by a therapeutically-effective amount of a drug; and/or (4) maintain the level of relief of one or more symptoms, or if symptoms were eliminated, maintain the non-existence of symptoms associated with a bacterial infection achieved by administration of a therapeutically-effective amount of a prodrug (e.g., of florfenicol ) of the present invention or some other appropriate drug. A prophylactically-effective amount also refers to that amount of a composition comprising a florfenicol prodrug of the present invention, or a florfenicol analog prodrug of the present invention, that will deliver florfenicol, or the florfenicol analog, in a sufficient plasma concentration to prohibit bacteria from accumulating in a susceptible organism in sufficient quantity to cause an infection.

An "aprotic solvent" refers to an organic solvent that does not include one or more hydrogen atoms bonded to an oxygen, nitrogen or sulfur atom, which hydrogen is capable of dissociation or participation in hydrogen bonding.

As used herein a "suitable" solvent refers to a solvent in which the reactants can dissolve and which does not adversely participate in the reaction, either by itself reacting with one or more components of the reaction mixture, or by interfering with the reaction of the components with one another. For any given reaction, selecting a suitable solvent is well within the ability of those skilled in the art and can be accomplished without undue experimentation.

The term "subject" refers to an animal species capable of being infected by a pathogenic bacterium, and in a particular embodiment includes humans. Appropriate animal subjects also include those in the wild, livestock (e.g., raised for meat, milk, butter, eggs, fur, leather, feathers and/or wool), beasts of burden, research animals, companion animals, as well as those raised for/in zoos, wild habitats and/or circuses.

In a particular embodiment a "subject" of the invention is a "food producing" animal. For purposes of the present invention, the term "food-producing" animal shall be understood to include all animals bred for consumption, or for consumables (e.g., dairy cows, egg-laying hens and the like) by humans and/or other animals. A non-limiting list of such animals include avians (chickens, turkeys, geese, duck, ostriches, etc.), bovines (e.g., cattle, dairy cows, buffalo), ovines (e.g., goats or sheep), porcines (e.g., hogs or pigs), equines (e.g., horses) etc., as well as aquatic animals including shellfish and fish such as trout or salmon, and other species raised or harvested for human consumption. For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping.

Examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed Plecostomus (*Plecostomus* spp).

| TAXON NAME | COMMON NAME |
| --- | --- |
| Salmonidae Family | |
| *Coregonus clupeaformis* | Lake whitefish |
| *Coregonus hoyi* | Bloater |
| *Oncorhynchus keta* | Chum salmon |
| *Oncorhynchus gorbuscha* | Pink salmon |
| *Oncorhynchus kisutch* | Coho salmon |
| | (silver salmon) |
| *Oncorhynchus masou* | cherry salmon (masou salmon) |
| *Oncorhynchus nerka* | Sockeye salmon |
| *Oncorhynchus tshawytscha* | (chinook salmon) |
| *Prosopium cylindraceum* | Round whitefish |
| *Oncorhynchus clarki* | Cutthroat trout |
| *Oncorhynchus mykiss* | Rainbow trout |
| *Salmo salar* | Atlantic salmon |
| *Salmo trutta* | Brown trout |
| *Salmo trutta* X *S. fontinalis* | Tiger hybrid-trout |
| *Salvelinus alpinus* | Arctic charr |
| *Salvelinus confluentus* | Bull trout |
| *Salvelinus fontinalis* | Brook trout |
| *Salvelinus Ieucomaenis* | Japanese charr (white spotted charr) |
| *Salvelinus malma* | Dolly varden (Miyabe charr) |

-continued

| TAXON NAME | COMMON NAME |
| --- | --- |
| Salvelinus namaycush | Lake trout |
| Thymallus thymallus | Grayling |
| Some Members of the Serranidae Family | |
| Centropristis ocyurus | Bank sea bass |
| Centropristis philadelphicus | Rock sea bass |
| Centropristis striata | Black sea bass |
| Diplectrum bivittatum | Dwarf sandperch |
| Diplectrum formosum | Sand perch |
| Epinephelus flavolimbatus | Yellowedge grouper |
| Epinephelus morio | Red grouper |
| Serranus phoebe | Tattler |
| Serranus tortugarum | Chalk bass |
| Some Members of the Sparidae family | |
| Archosargus probatocephalus | Sheepshead |
| Archosargus rhomboidalis | Sea bream |
| Calamus penna | Sheepshead porgy |
| Lagodon rhomboides | Pinfish |
| Pagrus Major | Red Sea bream |
| Sparus aurata | Gilthead Sea bream |
| Stenotomus chrysops | Scup |
| Some Members of the Cichlidae family | |
| Aequidens latifrons | Blue acara |
| Cichlisoma nigrofasciatum | Congo cichlid |
| Crenichichla sp. | Pike cichlid |
| Pterophyllum scalare | Angel fish |
| Tilapia mossambica | Mozambique mouth breeder |
| Oreochromis spp. | Tilapia |
| Sarotherodon aurea | Golden Tilapia |
| Some Members of the Centrarchidae family | |
| Ambloplites rupestris | Rock bass |
| Centrarchus macropterus | Flier |
| Elassoma evergladei | Everglades pigmy sunfish |
| Elassoma okefenokee | Okefenokee pigmy sunfish |
| Elassoma zonatum | Banded pigmy sunfish |
| Enneacanthus gloriosus | Bluespotted sunfish |
| Enneacanthus obesus | Banded sunfish |
| Lepomis auritus | Redbreast sunfish |
| Lepomis cyanellus | Green sunfish |
| Lepomis cyanellus X L. gibbosus | Green x pumpkinseed |
| Lepomis gibbosus | Pumpkinseed |
| Lepomis gulosus | Warmouth |
| Lepomis humilis | Orange-spotted sunfish |
| Lepomis macrochirus | Bluegill |
| Lepomis megalotis | Longear sunfish |
| Micropterus coosae | Shoal bass |
| Micropterus dolomieui | Smallmouth bass |
| Micropterus punctulatus | Spotted bass |
| Micropterus salmoides | Largemouth bass |
| Pomoxis annularis | White crappie |
| Pomoxis nigromaculatus | Black crappie |

In another embodiment, the subject is a companion animal. For purposes of the present invention, the term "companion" animal shall be understood to include housecats (feline), dogs (canine), rabbit species, horses (equine), rodents (e.g., guinea pigs, squirrels, rats, mice, gerbils, and hamsters), primates (e.g., monkeys) and avians, such as pigeons, doves, parrots, parakeets, macaws, canaries, and the like.

Other animals are also contemplated to benefit from the inventive florfenicol phosphate esters, including marsupials (such as kangaroos), reptiles (such as farmed turtles), game birds, swans, ratites and other economically important domestic animals.

As noted previously, florfenicol is sparingly soluble in water, i.e., to approximately 1 mg/mL. However, in commercial formulations, concentrations of 300 mg/mL or more are often desired. To achieve such concentrations, organic solvents in which florfenicol is readily soluble are used in formulations. Unfortunately, many of these solvents cause irritation that is sometimes quite severe when such florfenicol-containing compositions are administered to a subject by injection, a preferred mode of administration. The present invention supplies a solution to this problem by providing a florfenicol prodrug that has improved water solubility, and moreover, can be used in an effective and efficient in vivo delivery of florfenicol. Achieving this end, however, proved not to be a trivial matter.

Many possible florfenicol prodrugs, such as, for example, a glutarate ester of florfenicol, are quite water soluble, i.e., over several hundred milligrams per milliliter. Many of these prodrugs, however, do not readily deliver florfenicol in serum and therefore would not be expected to do so in vivo. For example, FIG. 1 shows that only approximately 6% of a glutarate ester of florfenicol hydrolyzes back to florfenicol in bovine serum and only about 3% does so in rat serum after 4 hours of contact.

Quite surprisingly, the florfenicol phosphate ester of the present invention was found to not only have excellent solubility in water, i.e., over 600 mg/mL, but also to convert to florfenicol efficiently and in substantial amounts. This is also shown in FIG. 1, where it can be seen that over four hours in rat serum and bovine serum, the sodium salt of florfenicol phosphate is converted to the extent of approximately 40% and 60%, respectively. These levels of conversion in vitro would be considered by those skilled in the art as good indicators of therapeutically-effective conversion in vivo. As predicted, substantial concentrations of florfenicol were detected in the plasma after the intravenous administration of a florfenicol phosphate ester of the present invention in cattle, dogs, and pigs (see FIGS. 2–4).

The florfenicol phosphate ester of the present invention, e.g., florfenicol prodrug, and/or salts thereof (or phosphate esters of the florfenicol analogs and/or salts thereof), can be administered to a subject by any conventional means, including orally, or by injection.

It is preferable to have the florfenicol prodrug in an aqueous ready-to-use solution, when injections are to be administered. In order to achieve maximal stability and shelf-life of the florfenicol prodrug in a solution, preferably the molar ratio of the base (e.g., a free amine) that is combined with the acid form of the florfenicol phosphate ester is maintained in the range of 0.6–1.4 in their aqueous solutions. It is more preferred to maintain this molar ratio in the 0.8–1.2 range in the aqueous solution. It is even more preferred to maintain this molar ratio in the 0.9–1.1 range in the aqueous solution. In a particular embodiment, the pH of the solution should be maintained at approximately pH 4.5.

The present invention may be better understood by reference to the following non-limiting examples, which are provided as exemplary of the invention. The following examples are presented in order to more fully illustrate embodiments of the invention and should in no way be construed as limiting the broad scope of the invention.

EXAMPLES

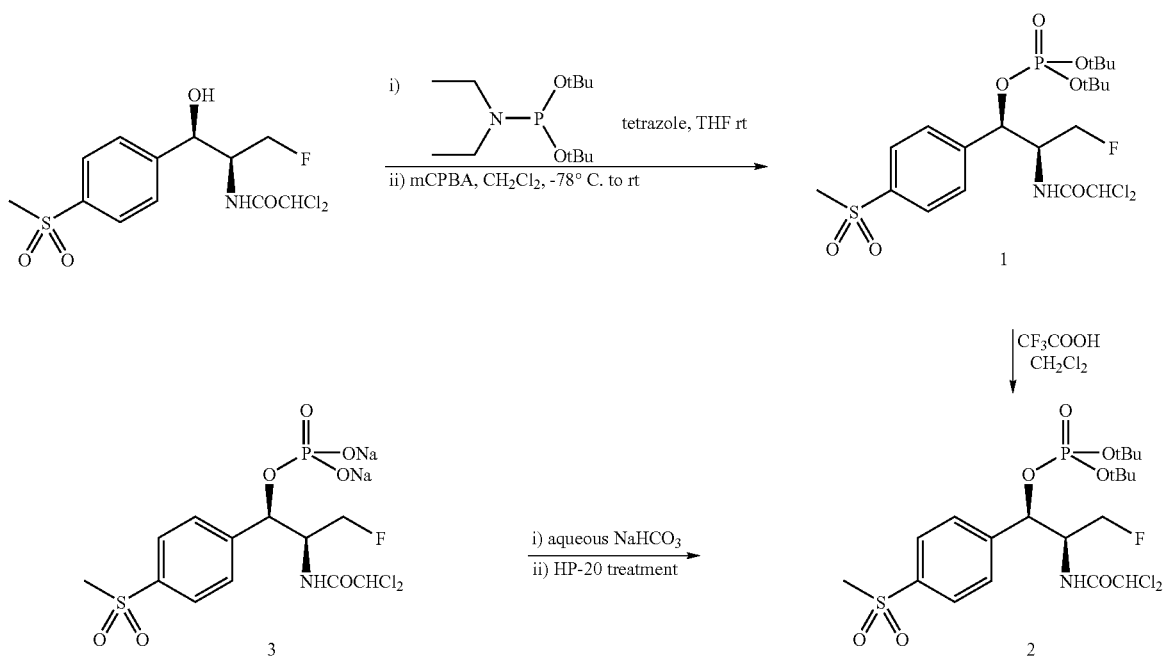

SCHEME 1
Synthesis of Florfenicol Phosphate Ester, Disodium Salt

Example 1

[1R,2S-1-(4-Methanesulfonylphenyl)-2-(2,2-dichloroacetylamino)-3-fluoropropyl]-di-tert-butyl phosphate (1)

To a solution of florfenicol (14.32 g, 40 mmol) and tetrazole (3.96 g, 56 mmol) in anhydrous tetrahydrofuran (THF, 70 mL) under nitrogen, was added, dropwise, N,N-diethyl di-tert-butyl phosphoramidite (12.8 mL, 46 mmol). The resulting solution was stirred at ambient temperature for 1.5 hours, during which time a fine precipitate formed. Stirring was continued for an additional 22.5 hours, after which the suspension was cooled to −78 °C. and a solution of m-chloroperbenzoic acid (75%, 12 g) in dichloromethane (60 mL) was added dropwise. The resulting solution was stirred at ambient temperature for 1.5 hours and then concentrated in vacuo. The residue was dissolved in ethyl acetate (200 mL) and washed with three 100 mL portions of saturated aqueous sodium bicarbonate. The organic layer was then dried over anhydrous sodium sulfate and concentrated in vacuo to yield a gum, which was purified by silica gel flash column chromatography to give 10.61 g of compound 1 as a white foam.

$^1$H NMR (d$_6$ DMSO, 400 MHz): δ 8.92 (d, 1H, J=9.2), 7.91 (d, 2H, J=8.5), 7.62 (d, 2H, J=8.5), 6.48 (s, 1H), 5.52 (dd, 1H, J=8.5, 3.2), 4.7–4.32 (m, 3H) 3.19 (s, 3H), 1.31 (s, 9H), 1.29 (s, 9H).

ESMS (negative mode, relative abundance shown in parentheses): m/z 208.80 (100), 491.66 (90), 493.54 (70). 547.68 (30), 549.51 (25, M$^+$).

HPLC: t$_R$ 11.2 min. purity 96.6% (Column: ACE 5 C18, 4.6×150 mm; mobile phase 0.1% aq. H$_3$PO$_4$/CH$_3$CN gradient).

Example 2

[1R,2S-1-(4-methanesulfonylphenyl)-2-(2,2-dichloroacetylamino(-3-fluoropropyl]phosphate (2)

To a solution of compound 1 (12.75 g, 23.2 mmol) in anhydrous dichloromethane (150 mL) under nitrogen, was added trifluoroacetic acid (15 mL), and the solution was stirred at ambient temperature for 2 hours. The solution was then concentrated in vacuo to yield a gum, which, upon trituration with diethyl ether, gave 9.97 g of compound 2 as a white solid.

$^1$H NMR (d$_6$ DMSO, 400 mHz): δ 8.81 (d, 1H, J=9.0), 7.87 (d, 2H, J=8.4), 7.63 (d, 2H, J=8.4), 6.43 (s, 1H), 5.58 (dd, 1H, J=9.6, 2.0), 4.80–4.3 (m, 3H), 3.18 (s, 3H).

ESMS (negative mode, relative abundance shown in parentheses): m/z 435.55 (100), 437.45 (75).

HPLC: t$_R$ 9.1 min, purity 91.9% (Column: ACE 5 C18, 4.6×150 mm, mobile phase 0.1% H$_3$PO$_4$/CH$_3$CN gradient).

Example 3

[1R,2S -1-(4-Methanesulfonylphenyl)-2-(2,2-dichloroacetylamino)-3-fluoropropyl]phosphate disodium salt (3)

The acid compound 2 (9.97 g, 22.8 mmol) was added in small portions to an aqueous solution of aqueous sodium bicarbonate (3.82 g, 45.5 mmol in 45 mL water). The resulting solution was run through an HP-20 resin column with water as the eluent. Fractions containing product were pooled and lyophilized to give 8.81 g of compound 3 as a white solid.

$^1$H NMR (D$_2$O, 400 mHz): δ 7.75 (d, 1H J=7.1), 7.57 (d, 2H, J=7.1), 6.03 (s, 1H), 5.30 (br d, 1H, J-9.7), 4.75 (ddd, 1H, J=45.5, 9.0, 4.3), 4.47 (dt, 1H, J=47, 9.0), 4.33 (br m, 1 h), 3.07 (s, 3H).

ESMS (negative mode, relative abundance shown in parentheses): m/z 435.60 (100), 437.49 (70).

HPLC: t$_R$ 9.2 min, purity 97.3% (Column: ACE 5 Ca8, 4.6×150 mm, mobile phase: 0.1% H$_3$PO$_4$/CH$_3$CN gradient).

Example 4

Conversion of Florfenicol Phosphate to Florfenicol in Serum

Florfenicol phosphate may be dissolved in a 0.1 M phosphate (KH$_2$PO$_4$) buffered medium of rat or bovine serum at 37° C. Then, 100 μL of the florfenicol phosphate-containing medium may be removed after at 0, 0.5, 1, 2, 3 and 4 hours, mixed with 100 μL acetonitrile (CH$_3$CN) and analyzed by column chromatography (Zorbax C8 column 4.6×15 cm, eluent: 0.1% H$_3$PO$_4$/CH$_3$CN) to determine the percent conversion of the prodrug to florfenicol.

Example 5

Conversion of Florfenicol Glutarate to Florfenicol in Serum

Florfenicol glutarate may be dissolved in a 0.1 M phosphate (KH$_2$PO$_4$) buffered medium of rat or bovine serum at 37° C. Then, 100 μL of the florfenicol glutarate-containing medium may be removed after at 0, 0.5, 1, 2, 3 and 4 hours, mixed with 100 μL acetonitrile (CH$_3$CN) and analyzed by column chromatography (Zorbax C8 column 4.6×15 cm, eluent: 0.1% H$_3$PO$_4$/CH$_3$CN) to determine the percent conversion of the prodrug to florfenicol.

Example 6

Measurement of Aqueous Solubility of the Phosphate Ester Prodrug of Florfenicol Successive aliquots of solid phosphate ester prodrug (sodium salt) were added to water with agitation. Addition was continued until mixing became difficult due to high viscosity, at which point all of the prodrug remained in solution. An aliquot of this solution (of known volume) was diluted with a known quantity of water and was analyzed by HPLC to determine the original concentration, which was found to be greater than 700 mg/mL.

Example 7

Stability of the Phosphate Prodrug in Aqueous Solutions

Although relatively stable in aqueous solutions, over prolonged periods of time the phosphate ester of florfenicol (Formula I) undergoes slow degradation resulting in the release of free florfenicol as well as the formation of cyclic phosphate diester. The formation of the cyclic diester occurs through the phosphate anion displacement of fluorine and requires participation of the phosphate di-anion, which is much more nucleophilic than the corresponding mono-anion. Therefore, the rate of formation of the cyclic diester is largely dependent on the pH of the solution or more generally, on the degree of the phosphate ionization. Heating a solution of the bis sodium salt of florfenicol phosphate prodrug results in almost quantitative conversion of the prodrug into cyclic diester. Satisfactory stability of aqueous solutions of the prodrug can be achieved when the amount close to one equivalent of either sodium hydroxide or ethanolamine is added to the concentrated aqueous solution of the florfenicol phosphate prodrug resulting in the pH range of approximately pH 4.5 to pH 5.5. However, even such small changes of pH result in noticeable differences of the amount of the cyclic phosphate diester formed.

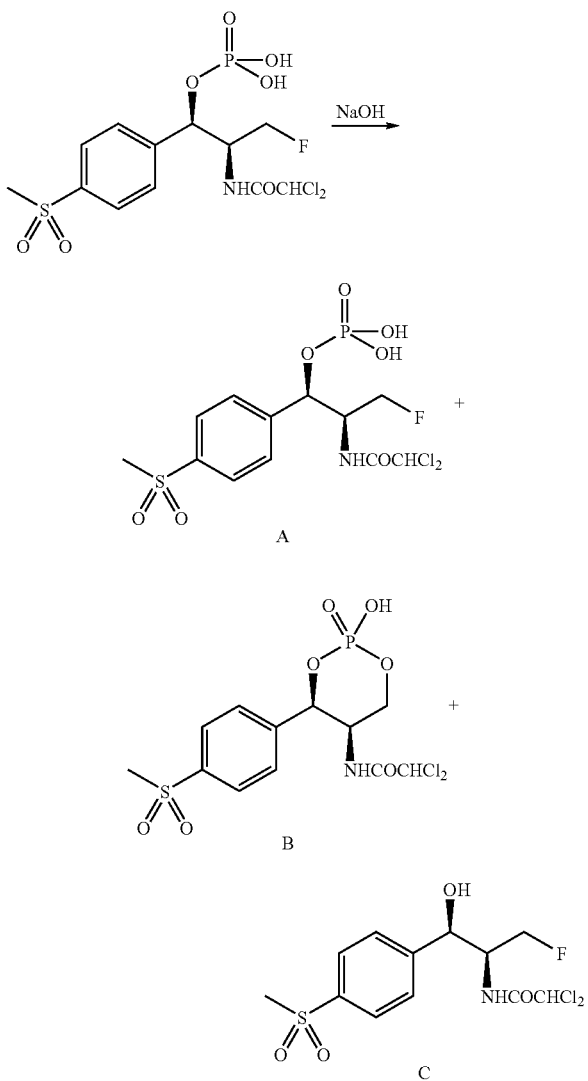

| pH | % Compound A | % Compound B | % Compound C |
|------|--------------|--------------|--------------|
| 4.54 | 94.40 | 0.17 | 1.02 |
| 4.95 | 93.38 | 0.37 | 1.01 |
| 5.53 | 93.06 | 1.41 | 0.93 |

An aqueous solution of the phosphate ester of florfenicol in the phosphate acid form containing 300 mg/mL of active florfenicol was heated at 40° C. for 30 days under nitrogen. Initial HPLC purity of the prodrug acid was 98.3% with no noticeable amounts of cyclic phosphate B and free florfenicol C.

Similar results were obtained when ethanolamine was used to adjust the pH of the solution:

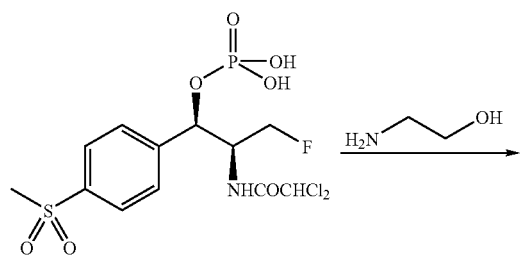

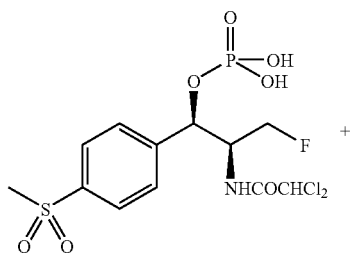

A

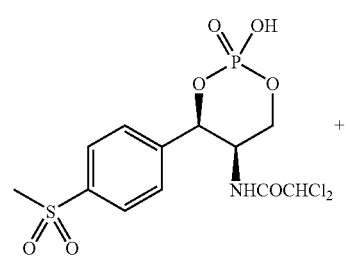

B

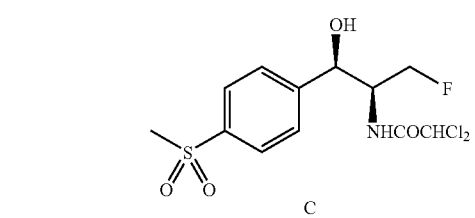

C

| pH | % Compound A | % Compound B | % Compound C |
| --- | --- | --- | --- |
| 4.48 | 93.43 | 0.18 | 0.92 |
| 5.03 | 95.83 | 0.58 | 0.86 |
| 5.51 | 93.83 | 1.25 | 0.70 |

An aqueous solution of prodrug phosphate acid containing 300 mg/mL of active florfenicol was heated at 40° C. for 30 days under nitrogen. Initial HPLC purity of the prodrug acid was 98.3% with no noticeable amounts of cyclic phosphate B and free florfenicol C.

The florfenicol phosphate prodrug is less stable below pH 4 or at neutral or higher pH ranges. In addition, increased ionic strength reduces the aqueous stability of florfenicol phosphate prodrug in solution.

Example 8

Conversion of Florfenicol Phosphate to Florfenicol in Cattle

Figure 2:
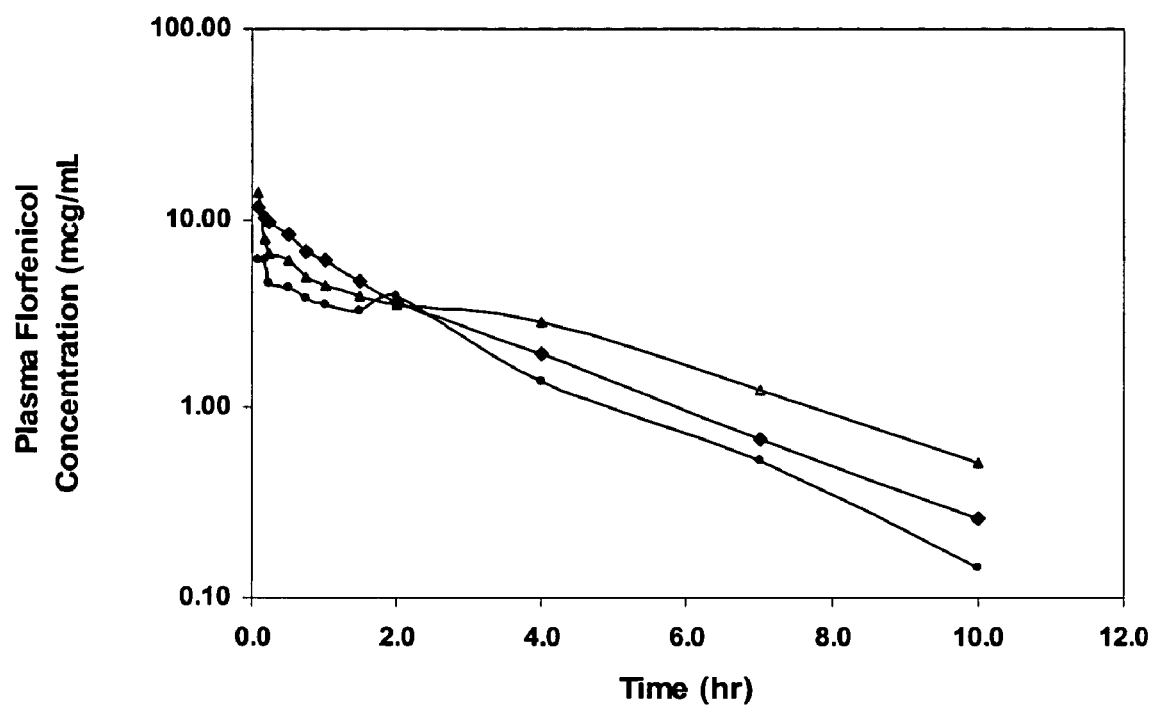
FIG. 2 shows a graphic presentation of florfenicol concentrations detected in the plasma of calves following intravenous administration of florfenicol phosphate ester. The plot depicts florfenicol concentrations detected in the plasma of three calves following intravenous administration of florfenicol phosphate ester prodrug at a dose of approximately 10 mg/kg of calf body weight. Each symbol denotes the data from a different calf.

Florfenicol phosphate was dissolved in water to a concentration of approximately 600 mg/mL. The solution was then injected intravenously into three calves weighing 69 to 121 kg to provide a dose of approximately 10 mg/kg of calf body weight. Plasma samples were collected after drug administration and analyzed for concentrations of florfenicol by HPLC-MS/MS. Plasma florfenicol concentrations increased rapidly following treatment (FIG. 2). These data demonstrate that the prodrug is rapidly cleaved to florfenicol in cattle.

Example 9

Conversion of Florfenicol Phosphate to Florfenicol in Dogs

Figure 3:
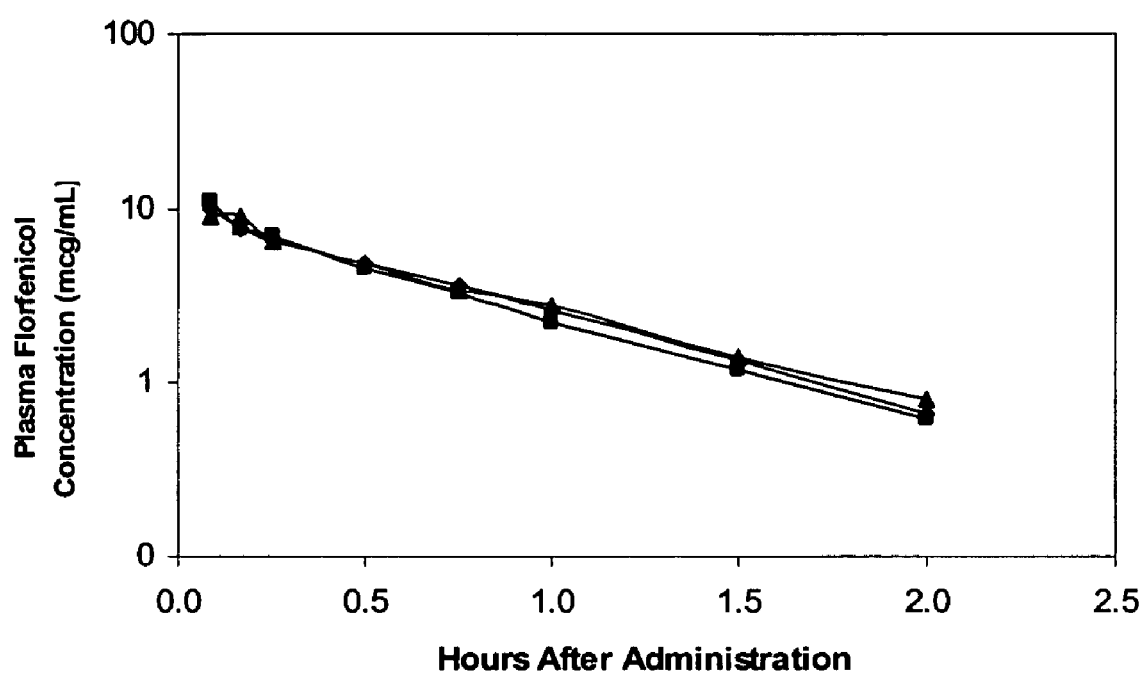
FIG. 3 shows a graphic presentation of florfenicol concentrations detected in the plasma of dogs following intravenous administration of florfenicol phosphate ester. The plot depicts florfenicol concentrations in the plasma of three dogs following intravenous administration of the florfenicol phosphate ester prodrug at a dose of approximately 11.1 mg/kg of body weight, which equates to a florfenicol equivalent dose of 8.3 mg/kg. Each symbol denotes the data from a different dog.

Florfenicol phosphate was dissolved in water to a concentration of approximately 200 mg/mL. The solution was then injected intravenously into three dogs weighing 9 to 15 kg to provide a dose of approximately 11 mg/kg of body weight. Plasma samples were collected after drug administration and analyzed for concentrations of florfenicol by HPLC-MS/MS. Plasma florfenicol concentrations increased rapidly following treatment (FIG. 3). These data demonstrate that the prodrug is rapidly cleaved to florfenicol in dogs.

Example 10

Conversion of Florfenicol Phosphate to Florfenicol in Swine

Figure 4:
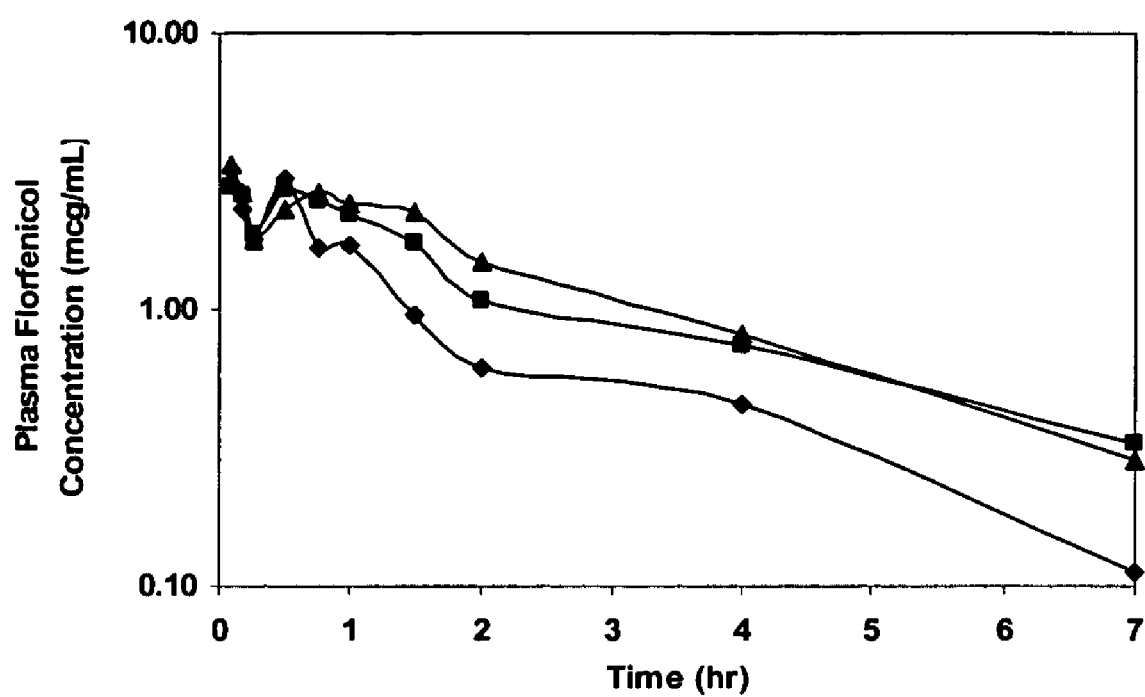
FIG. 4 is a graphic presentation of florfenicol concentrations in the plasma of pigs following intravenous administration of florfenicol phosphate ester. The plot depicts florfenicol concentrations detected in the plasma of three pigs following intravenous administration of the florfenicol phosphate ester prodrug at a dose of approximately 6.7 mg/kg of body weight, which equates to a florfenicol equivalent dose of 5 mg/kg. Each symbol denotes the data from a different pig.

Florfenicol phosphate was dissolved in water to a concentration of approximately 300 mg/mL. The solution was then injected intravenously into three pigs weighing 10 to 15 kg to provide a dose of approximately.6.7 mg/kg of body weight. Plasma samples were collected after drug administration and analyzed for concentrations of florfenicol. Plasma florfenicol concentrations increased rapidly following treatment (FIG. 4). These data demonstrate that the prodrug is rapidly cleaved to florfenicol in pigs.

Many modifications and variations of the present invention can be made without departing from its spirit and scope, as will be apparent to those skilled in the art. The specific embodiments described herein are offered by way of example only, and the invention is to be limited only by the terms of the appended claims, together with the full scope of equivalents to which such claims are entitled.

What is claimed:

1. A florfenicol phosphate ester having the chemical structure

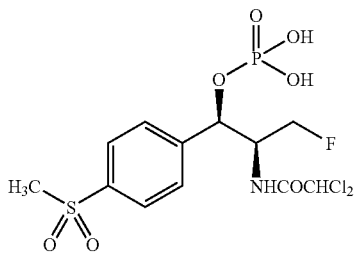

or a salt thereof.

2. The florfenicol phosphate ester of claim 1 that is a florfenicol prodrug having the chemical structure:

19

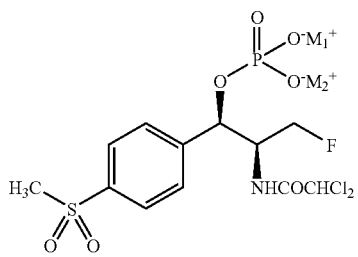

wherein $M_1^+$ and $M_2^+$ are $H^+$ or a pharmaceutically-acceptable mono-cation, or taken together, are a pharmaceutically-acceptable di-cation.

3. The florfenicol prodrug of claim 2, wherein $M_1^+$ and $M_2^+$ are independently selected from the group consisting of $H^+$, $Na^+$, $NH_4^+$, and $K^+$.

4. The florfenicol prodrug of claim 3, wherein $M_{1+}$ or $M_2^+$ is $H^+$ and $M_2^+$ or $M_1^+$, which is not $H^+$, is $Na^+$.

5. The florfenicol prodrug of claim 3, wherein $M_1^+$ and $M_2^+$ are both $Na^+$.

6. The florfenicol prodrug of claim 2, wherein $M_1^+$ and $M_2^+$ are independently selected from the group consisting of $H^+$ and a protonated amine.

7. The florfenicol prodrug of claim 6, wherein the protonated amine is $NR^1R^2R^3H^+$, and wherein $R^1$, $R^2$, and $R^3$ are independently selected to be either H, methyl, ethyl, propyl, isopropyl, —$CH_2CH_2OH$ and —$CH_2C(CH_2OH)_3$.

8. The florfenicol prodrug of claim 7, wherein the protonated amine is selected from the group consisting of:

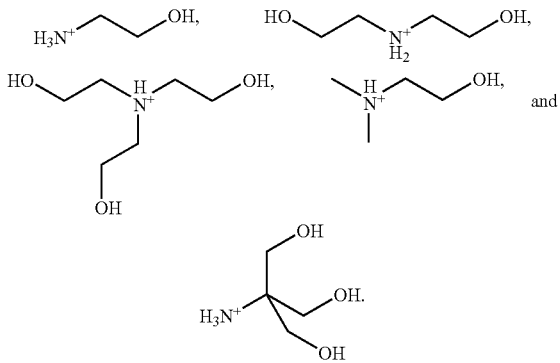

and

9. The florfenicol prodrug of claim 8, wherein the protonated amine is:

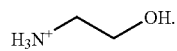

10. The florfenicol prod rug of claim 7,
wherein $R^1$ is either H. methyl, ethyl, propyl, isopropyl, —$CH_2CH_2OH$ and —$CH_2C(CH_2OH)_3$; and
wherein $R^2$ and $R^3$ are linked to form a five or six membered ring.

11. The florfenicol prodrug of claim 10, wherein the five or six membered ring are selected from the group consisting of pirolidine, piperidine, or morpholine.

12. The florfenicol prodrug of claim 2, wherein $M_1^+$ and $M_2^+$ comprise respectively, $H^+$ and a mono-cationic form of a dibasic aminoacid.

20

13. The florfenicol prodrug of claim 2, wherein $M_1^+$ and $M_2^+$ are independently selected to be either $H^+$, meglumine, benzocaine, or procaine.

14. The florfenicol prodrug of claim 2, wherein $M_1^+$ and $M_2^+$ are taken together, and selected from the group consisting of $Ca^{+2}$, $Mg^{+2}$, a bis-protonated diamine, and a di-cationic form of a dibasic amino acid.

15. A pharmaceutical composition comprising the florfenicol prodrug of claim 2 in a pharmaceutically acceptable carrier.

16. The pharmaceutical composition of claim 15, wherein the pharmaceutically acceptable carrier is an aqueous solution.

17. The pharmaceutical composition of claim 16, which comprises a mixture of two or more salts of the florfenicol prodrug.

18. The pharmaceutical composition of claim 16, wherein the pH of the aqueous solution is between pH 3.5 and pH 6.5.

19. The pharmaceutical composition of claim 18, wherein the pH of the aqueous solution is between pH 4.0 and pH 6.

20. The pharmaceutical composition of claim 19, wherein the pH of the aqueous solution is between pH 4.5 and pH 5.5.

21. The pharmaceutical composition of claim 16, wherein the florfenicol phosphate ester is a mixture of a salt form of the florfenicol phosphate ester and an acid form of the florfenicol phosphate ester; and wherein a molar ratio of the base that is combined with the acid form of the florfenicol phosphate ester is in the range of 0.6–1.4.

22. The pharmaceutical composition of claim 21, wherein the molar ratio is in the range of 0.8–1.2.

23. The pharmaceutical composition of claim 22, wherein the molar ratio is in the range of 0.9–1.1.

24. A compound of the chemical formula:

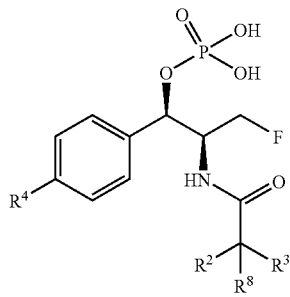

or a salt thereof;
wherein $R^2$ and $R^3$ are independently selected from the group consisting of hydrogen, (1C–4C)alkyl, halo, —$CF_3$, —$NH_2$, —CN and $N_3$;
wherein $R^4$ is selected from the group consisting of:

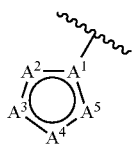 and 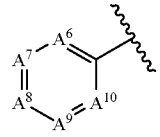

wherein $A^1$ is carbon or nitrogen, and carbon atoms in the ring are independently substituted with an entity selected from the group consisting of hydrogen, (1C–4C)alkyl, (3C–6C)cycloalkyl, (1C–4C)alkylO—, —CF₃, —OH, —CN, halo, (1C–4C)alkylSO—, (1C–4C)alkylSO₂—, NH₂SO₂—, (1C–4C)alkyl-NHSO₂—, ((1C–4C)alkyl)₂NSO₂—, —NH₂, (1C–4C)alkylNH—, ((1C–4C)alkyl)₂N—, (1C–4C)alkylSO₂NH—, (1C–4C)alkylC(O)—, (3C–6C)cycloalkylC(O)—, (1C–4C)alkylOC(O)—, (1C–4C)alkylC(O)NH—, —C(O)NH₂, (1C–4C)alkylNHC(O)— and ((1C–4C)alkyl)₂NC(O)—, wherein any of the alkyl groups within the substituents may be unsubstituted or substituted with a group selected from halo and hydroxy;

wherein A², A³, A⁴, and A⁵ are independently selected from the group consisting of carbon, nitrogen, oxygen and sulfur, provided that at least one of A¹–A⁵ is not carbon, that the total number of nitrogen, oxygen and sulfur atoms in the ring does not exceed 4 and that the ring is aromatic; and wherein if A¹ is carbon and the ring does not contain oxygen or sulfur, one of the nitrogen atoms may optionally be substituted with an entity selected from the group consisting of (1C–4C)alkyl, (1C–4C)alkylSO₂— and —NH₂; and wherein A⁶, A⁷, A⁸, A⁹ and A¹⁰ are independently selected from the group consisting of carbon, nitrogen and

provided that only one of A⁶–A¹⁰ at a time can be

and that one, two, or three of the A⁶–A¹⁰ atoms are nitrogen; and wherein the carbon atoms in the ring are independently substituted with an entity selected from the group consisting of hydrogen, (1C–4C)alkyl, (3C–6C)cycloalkyl, (1C–4C)alkylO—, —CF₃, —OH, —CN, halo, (1C–4C)alkylSO—, (1C–4C)alkylSO₂—, NH₂SO₂—, (1C–4C)alkylNHSO₂—, ((1C–4C)alkyl)₂NSO₂—, —NH₂, (1C–4C)alkylNH—, ((1C–4C)alkyl)₂N—, (1C–4C)alkylSO₂NH—, (1C–4C)alkylC(O)—, (3C–6C)cycloalkylC(O)—, (1C–4C)alkylOC(O)—, (1C–4C)alkylC(O)NH—, —C(O)NH₂, (1C–4C)alkylNHC(O)—, ((1C–4C)alkyl)₂NC(O)— and —OCH₂O—, wherein the oxygen atoms with the —OCH₂O— substituent being bonded to adjacent ring carbon atoms, and wherein any of the alkyl groups within any of the substituents may be unsubstituted or substituted with a group selected from halo and hydroxy; and wherein R⁸ is hydrogen in all compounds, except when R² and R³ are both F, in which case R⁸ is hydrogen or F; and, the compound is either a racemate having the relative stereochemistry shown or is substantially enantiomerically pure and has the absolute stereochemistry shown.

25. A pharmaceutical composition comprising the compound of claim 24 in a pharmaceutically acceptable carrier.

26. A method for the synthesis of the acid form of a florfenicol phosphate ester having the chemical structure:

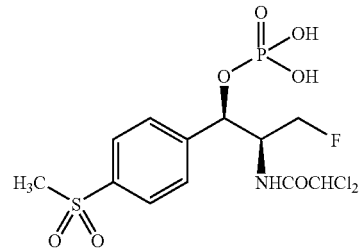

comprising the steps of:
(a) reacting florfenicol with di-tert-butylphosphoramidite in the presence of tetrazole in a first suitable solvent to yield a first intermediate;
(b) adding to the first intermediate an oxidant in a second suitable solvent to yield a second intermediate;
(c) isolating the second intermediate;
(d) dissolving the second intermediate in a third suitable solvent; and
(e) reacting the second intermediate with trifluoroacetic acid to yield the acid form of the florfenicol phosphate ester.

27. The method of claim 26 further comprising the step of isolating the acid form of the florfenicol phosphate ester.

28. A method for the synthesis of a salt form of a florfenicol phosphate ester having the chemical structure:

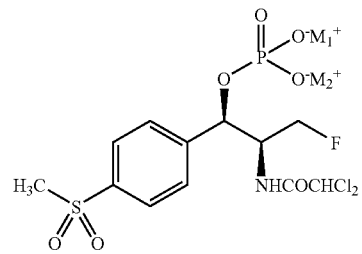

wherein $M_1^+$ and $M_2^+$ are a pharmaceutically-acceptable mono-cation, or taken together, are a pharmaceutically-acceptable di-cation, wherein said method comprises combining the isolated acid form of the florfenicol phosphate ester of claim 27 with an aqueous solution of a base comprising a pharmaceutically-acceptable cation or di-cation to yield a form of the florfenicol phosphate ester as the salt of the cation or di-cation.

29. The method of claim 28, wherein the pharmaceutically-acceptable cation or di-cation are a protonated amine or a bis-protonated diamine respectively.

30. The method of claim 28, further comprising the step of isolating the salt form of the florfenicol phosphate ester.

* * * * *

UNITED STATES PATENT AND TRADEMARK OFFICE
CERTIFICATE OF CORRECTION

PATENT NO. : 7,153,842 B2  Page 1 of 1
APPLICATION NO. : 11/016794
DATED : December 26, 2006
INVENTOR(S) : Hecker et al.

It is certified that error appears in the above-identified patent and that said Letters Patent is hereby corrected as shown below:

(Column 19, line 20)

Change "$M_{1+}$" to --$M_1^+$--.

Signed and Sealed this

Twenty-seventh Day of March, 2007

JON W. DUDAS
*Director of the United States Patent and Trademark Office*